United States Patent
Wermes et al.

(10) Patent No.: US 11,543,686 B2
(45) Date of Patent: Jan. 3, 2023

(54) MEASURING INSTRUMENT FOR MEASURING PARAMETERS NECESSARY FOR PRODUCING SPECTACLES

(71) Applicant: INTERACTIF VISUEL SYSTEME (I V S), Clichy (FR)

(72) Inventors: Jonathan Wermes, Paris (FR); David Encaoua, Carrieres sur Seine (FR)

(73) Assignee: INTERACTIF VISUEL SYSTEME (I V S)

( * ) Notice: Subject to any disclaimer, the term of this patent is extended or adjusted under 35 U.S.C. 154(b) by 0 days.

(21) Appl. No.: 17/278,926

(22) PCT Filed: Sep. 24, 2019

(86) PCT No.: PCT/EP2019/075746
§ 371 (c)(1),
(2) Date: Mar. 23, 2021

(87) PCT Pub. No.: WO2020/064758
PCT Pub. Date: Apr. 2, 2020

(65) Prior Publication Data
US 2022/0043285 A1 Feb. 10, 2022

(30) Foreign Application Priority Data

Sep. 24, 2018 (FR) ...................................... 1858645

(51) Int. Cl.
*H04N 5/232* (2006.01)
*A61B 3/14* (2006.01)
(Continued)

(52) U.S. Cl.
CPC .............. *G02C 13/003* (2013.01); *A61B 3/14* (2013.01); *H04N 5/23203* (2013.01); *A61B 3/0058* (2013.01)

(58) Field of Classification Search
None
See application file for complete search history.

(56) References Cited

U.S. PATENT DOCUMENTS

| 5,617,155 A | 4/1997 | Ducarouge et al. |
| 2009/0021693 A1* | 1/2009 | Sessner ................ G02C 13/005 351/204 |

(Continued)

FOREIGN PATENT DOCUMENTS

| FR | 2719463 A1 | 11/1995 |
| FR | 2950984 A1 | 4/2011 |

(Continued)

OTHER PUBLICATIONS

International Search Report for Application No. PCT/EP2019/075746 dated Nov. 26, 2019, pp. 1-4.

*Primary Examiner* — Samuel D Fereja
(74) *Attorney, Agent, or Firm* — Lerner, David, Littenberg, Krumholz & Mentlik, LLP (57) ABSTRACT

The invention concerns a method for measuring parameters necessary for producing corrective spectacles using an instrument (1) comprising the following steps: S1: positioning the wearer at a predefined distance from the frame (2) of the instrument (1), S2: placing a screen (5) of the instrument (1) opposite the wearer and displaying at least one image, S3: placing the frame of the corrective spectacles on the face of the wearer, S4: substituting the screen (5) with a one-way mirror (4) of the instrument, S5: taking the measurements.

10 Claims, 5 Drawing Sheets

(51) Int. Cl.
*G02C 13/00* (2006.01)
*A61B 3/00* (2006.01)

(56) References Cited

U.S. PATENT DOCUMENTS

| | | |
|---|---|---|
| 2012/0257162 A1 | 10/2012 | Encaoua et al. |
| 2015/0109577 A1 | 4/2015 | Haddadi et al. |
| 2015/0146168 A1* | 5/2015 | Divo .................. A61B 3/103 |
| | | 351/204 |
| 2017/0322430 A1 | 11/2017 | Fayolle et al. |
| 2018/0048754 A1* | 2/2018 | Pont .................... H04N 5/335 |

FOREIGN PATENT DOCUMENTS

| | | | | |
|---|---|---|---|---|
| FR | 2978841 A1 * | 2/2013 | ............ | G03B 15/00 |
| WO | 2014006341 A1 | 1/2014 | | |
| WO | 2016075372 A1 | 5/2016 | | |

\* cited by examiner

MEASURING INSTRUMENT FOR MEASURING PARAMETERS NECESSARY FOR PRODUCING SPECTACLES

CROSS-REFERENCE TO RELATED APPLICATIONS

The present application is a national phase entry under 35 U.S.C § 371 of International Application No. PCT/EP2019/075746 filed Sep. 24, 2019, which claims priority from French Application No. 1858645 filed Sep. 24, 2018, all of which are hereby incorporated herein by reference.

FIELD OF THE INVENTION

The invention concerns the field of measurements usually made by an optician with a view to the customization of corrective ophthalmic lenses and their mounting on a frame. More specifically, the invention concerns the field of optical metrology, that is to say the measurement of the various parameters necessary for the production of glasses.

TECHNOLOGICAL BACKGROUND

Optical stores usually lack space: their walls and their available spaces are mostly occupied by glass display racks, mirrors allowing the customers to try on the glasses as well as screens broadcasting various information, in particular product presentations, often for advertising purposes or to keep the customers waiting. This lack of space is a major obstacle to the deployment of a measuring instrument for measuring vision parameters of a wearer, of the type of the measuring instrument described in document FR2950984 or the ACTIVISU column proposed by the Applicant. Such a column indeed takes the place of a display rack, a mirror and/or a screen.

To overcome this problem, the ACTIVISU column comprises, for example, a large one-way mirror, behind which the camera is placed. The wearer can then look at himself in the mirror to try on a frame or have her picture taken, and then see himself in the mirror after putting on her corrective glasses. A screen used for the control of the column and for different monitoring operations and interactions when taking measurements is fixed next to the column. When the column is not used to make measurements, the screen can broadcast information or animations, like the other screens in the store.

However, this screen is small compared to the advertising screens and therefore draws attention less easily. In addition, due to its position on the column, it conceals part of a wall-mounted glass display rack or prevents the fixing of such a display rack.

Furthermore, during the measurements for the customization of the corrective glass lenses and the centering/mounting of these lenses in the frame, the subject is asked to stand in front of the mirror and to look at his reflection in the latter. During these measurements, the subject must look straight ahead (while globally aiming the bridge of her frame in the mirror or the center of her face if he cannot distinguish the bridge), horizontally, at a distance generally comprised between three and five meters. This placement of the wearer relative to the measuring instrument is important for obtaining quality measurements. However, it appears that the measurements obtained are often distorted due to a wrong right-left orientation of the face of the wearer (measurement error on the heading angle), to intimidation of the wearer related to the mirror or to the environment and distorting the wearer's natural posture (measurement errors on the tilt (pantoscopic) angle and possibly the heading angle) or to a poor orientation relative to the displacement to arrive in front of the column.

SUMMARY OF THE INVENTION

An objective of the invention is therefore to propose an instrument for measuring parameters necessary for the production of corrective glasses capable of proposing a solution to the problems identified above, and which particularly allow helping the wearer to position himself correctly relative to the measuring instrument, during the measurements, without presenting a hindrance for the optical store or reducing the space available for the frame display racks, the mirrors and the advertising screens.

For that purpose, the invention proposes a measuring instrument for measuring parameters necessary for the production of corrective glasses for a wearer comprising:
  a frame,
  at least one at least partially light-blocking screen capable of at least partially reflecting light, mounted on the frame,
  at least one screen mounted on the frame,
  at least one image acquisition device mounted on the frame so as to be concealed by the at least partially light-blocking screen, and
  substitution means to reversibly substitute the screen with the at least partially light-blocking screen, so as to present the screen to the wearer during a positioning phase wherein the wearer is positioned with respect to the instrument, and the at least partially light-blocking screen with the screen during a measurement phase.

Some preferred but non-limiting characteristics of the measuring instrument are as follows, taken individually or in combination:
  the at least partially light-blocking screen comprises a one-way mirror,
  the frame further comprises a foot configured to hold the instrument in a stable manner on a ground, a first face and a second face distinct from each other, the at least partially light-blocking screen being fixed on the first face while the screen is fixed on the second face, and in which the substitution means comprise a pivot link configured to rotate the frame relative to the foot about an axis of rotation so that a rotation of the frame about the axis of rotation has the effect of placing the at least partially light-blocking screen or the screen in front of the wearer.
  the measuring instrument further comprises at least an abutment and/or an encoder configured to limit a travel of the frame about the axis of rotation.
  the substitution means comprise sliders configured so that one among the at least partially light-blocking screen or the screen is slidably mounted on the frame so as to conceal or reveal the other among the at least partially light-blocking screen or the screen.
  the measuring instrument further comprises a wireless monitoring device configured to send instructions to the image acquisition device and to the screen.
  the measuring instrument further comprises a storage space formed in the frame and configured to receive the monitoring device.
  a height of the screen is comprised between 30% and 100% of a height of the at least partially light-blocking screen.
  a height of the frame is comprised between 1.80 m and 2.20 m, a height of the at least partially light-blocking screen is comprised between 0.90 m and 2.0 m, preferably between 0.90 m and 1.60 m, and a height of the screen is comprised between 0.30 m and 1.60 m According to a second aspect, the invention also proposes a method for taking measurements of parameters necessary for the production of corrective glasses using an instrument as described above, comprising the following steps:

S1: positioning the wearer at a predefined distance from the frame of the instrument, S2: placing the screen in front of the wearer and displaying at least one image, S3: placing the frame of the corrective glasses on the face of the wearer, S4: substituting the screen with the at least partially light-blocking screen, S5: taking the measurements.

Optionally, step S4 is carried out by rotation of the frame relative to a foot of the instrument about an axis of rotation or by sliding of one among the screen or the at least partially light-blocking screen.

BRIEF DESCRIPTION OF THE DRAWINGS

Other characteristics, aims and advantages of the present invention will become more apparent upon reading the following detailed description and in relation to the appended drawings given by way of non-limiting examples and in which.

DETAILED DESCRIPTION OF ONE EMBODIMENT

A measuring instrument 1 for measuring parameters necessary for the production of corrective glasses of a wearer comprises:
- a frame 2 comprising a foot 3 configured to be put on the ground and stand, substantially vertically, in a stable manner,
- at least one at least partially light-blocking screen 4 capable of at least partially reflecting light and at least one screen 5, mounted on the frame 2,
- at least one image acquisition device 6 mounted on the frame 2 so as to be concealed by the one-way mirror 4.

In the following, the invention will be described more particularly in the case where the at least partially light-blocking screen 4 comprises a one-way mirror. However, this is not limiting, the at least partially light-blocking screen 4 being able to comprise any type of screen capable of concealing the image acquisition device 6, while reflecting light sufficiently so that the wearer can see his reflection in the screen. For example, screen 4 may comprise any semi-reflector capable of blocking at least 50% of the light.

In a manner known per se, the image acquisition device 6 may comprise a video camera, an infrared camera, a digital photographic apparatus, a scanner or any other means. Preferably, the image acquisition device 6 is configured to capture images in the visible spectrum (color camera for example). This image acquisition device 6 is placed in the upper region of the frame 2, in a plane of symmetry of the frame 2 (that is to say by being generally centered relative to the right and left edges of the frame 2) so to be able to be easily positioned in front of the face of the wearer.

When appropriate, in order to adapt the position of the image acquisition device 6 to the size of the wearer, the latter can be movably mounted in translation on one or more sliders. The displacement of the image acquisition device 6 along the sliders can be actuated by a suitable motor, for example a stepper motor in order to obtain an accurate positioning relative to the face of the wearer. As a variant, it is all or part of the frame 2 (for example its upper part on which the image acquisition device 6, the one-way mirror 4 and the screen 5 are mounted) that is displaced by such a motor along sliders so as to simultaneously displace all the equipment of the instrument 1.

Optionally, the instrument 1 can also comprise an electromechanical brake in order to hold the image acquisition device 6 in position after its displacement by the motor, which allows eliminating the holding currents.

The one-way mirror 4 is placed in front of the image acquisition device 6, in order to simultaneously allow the wearer to see himself in the one-way mirror 4 and the image acquisition device 6 to acquire images of the wearer.

The instrument 1 further comprises a processing unit comprising processing means, for example a computer or a server having processing means and a memory, adapted to execute the method for taking measurements S which will be described in more detail below. The processing means can for example comprise a computer of the processor, microprocessor, microcontroller, etc. type, The instrument 1 also comprises control means 7 (touch screen, keyboard, mouse, buttons, etc.). In one embodiment, the control means 7 comprise a wireless, and therefore portable, tablet equipped with a touch screen 5 which can be grasped by the operator in order to control the instrument 1 and monitor the different pieces of equipment that compose it. The tablet 7 advantageously replaces the monitor screen 5 usually fixed on the frame 2 of the conventional measuring instruments 1 which, in addition to being bulky and encroaching on the space available for the frame display racks, could hinder or constrain the wearer by imposing the operator in his field of vision.

When appropriate, a space for storing the tablet 7 may be provided in the frame 2, for example in a lateral face thereof.

The screen 5 for its part can be of the liquid crystal screen, LED (light-emitting diodes) screen or any other high-definition screen type. Preferably, the height $h_1$ of the screen 5 is comprised between 30% and 100% of the height $h_2$ of the one-way mirror 4. It is meant by "height" of an element of the instrument 1 the distance along a substantially vertical axis, when the frame 2 is placed in a stable manner on the ground, between a lower limit and an upper limit of the element. Typically, the height $h_3$ of the frame 2 can be comprised between 1.80 m and 2.20 m. The height $h_2$ of the mirror can then be comprised between 90 cm and 2.0 m, preferably between 90 cm and 1.60 m, while the height h1 of the screen 5 can be comprised between 30 cm and 1.60 m. Due to its large size, the screen 5 can therefore be used as an effective advertising broadcasting tool and allows great interactivity with the wearer during the positioning and placement phases S1 to S3 (which will be detailed later).

The screen can furthermore occupy all or part of a width of the frame 2.

In order to help the wearer to position himself correctly relative to the measuring instrument 1, without reducing the space available in an optical store, the instrument 1 further comprises reversible means 8 for substituting the screen 5 by the one-way mirror 4 so as to present the screen 5 to the wearer during the positioning S1, placement S2, S3 phases and apart from the measurement, and to substitute for this screen 5 the one-way mirror 4 during the phase of taking measurements S5.

In this way, the frame 2 comprises a first configuration, in which the screen 5 is presented to the wearer in order to relax his, to bring him into a natural posture not constrained by his environment, to perform preliminary operations (manual entry of data relating to the wearer or to the frame, etc.). For example, an animation presenting the rest of the procedure of taking measurements and presenting what is expected from the wearer during this procedure, can be displayed to the wearer on the screen 5. During this phase, the wearer can wear his corrective glasses, which can help him improve his positioning relative to the screen 5—and therefore to the one-way mirror 4 and to the image acquisition device 6.

The frame 2 comprises a second configuration, in which the one-way mirror 4 is presented to the wearer and the measurements are made, by substituting the one-way mirror 4 for the screen 5. The wearer does not need to move and must simply put on the frame for which measurements are to be made. When appropriate, an accessory can be placed on the frame in order to facilitate the measurements, the wearer is then always in a comfortable position and the measurements can be made.

It will be noted that, thanks to the substitution means 8, the screen 5 may have served, for example, as an advertising medium before starting taking measurements. The instrument 1 therefore did not encroach on the areas available in the optical store.

The substitution means 8 are further configured to substitute the screen 5 for the one-way mirror 4 once the measurements have been taken by the operator (reversible means).

In a first embodiment, the reversible substitution of the one-way mirror 4 for the screen 5 can be carried out by rotation of the frame 2 about an axis of rotation X, which can for example be substantially vertical.

Figure 3:
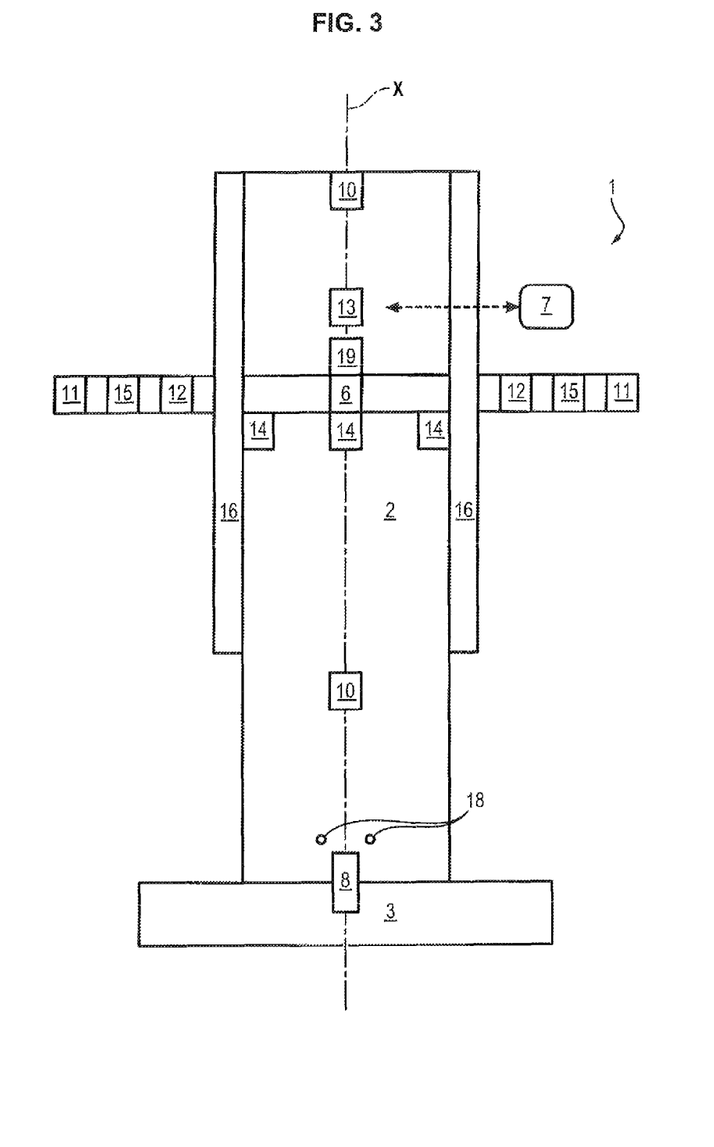
FIG. 3 is a schematic view which represents different possible pieces of equipment for a measuring instrument according to one embodiment of the invention, the one-way mirror having been omitted to simplify the reading of the figure.

In this embodiment, the one-way mirror 4 is then fixed on a first face 2a of the frame 2 while the screen 5 is fixed on a second face 2b of the frame 2, which is distinct from the first face 2a. For example, the first face 2a and the second face 2b can be substantially parallel and opposite to each other, on either side of the frame 2. The substitution means 8 then comprise a pivot link (see FIG. 3) extending between the foot 3 of the instrument 1 and the frame 2 and configured to rotate the frame 2 about the axis of rotation X relative to the foot 3 such that a rotation of the frame 2 about the axis of rotation X has the effect of presenting either of the faces of the frame 2, and therefore of placing the one-way mirror 4 or the screen 5 to the wearer, without risking to displace the instrument 1 relative to the wearer. It will indeed be noted that rotating the frame 2 by lifting it and by making it turn on itself manually, or by making it roll on the ground, presents the risk of distorting the positioning of the wearer relative to the instrument 1 and therefore degrading the measurements since the operator cannot guarantee that the mirror has actually taken the same position relative to the wearer as the screen 5. This also disturbs the wearer, who risks changing his position during the operation of displacement of the instrument 1 by the operator.

Such a substitution is also reversible, insofar as it suffices to rotate the frame 2 in the opposite direction or to continue the rotation in order to replace the screen 5 in front of the wearer.

In one embodiment, the instrument 1 further comprises a motor, configured to rotate the frame 2 about its axis of rotation X. The motor may for example be of the stepper type in order to allow accurate positioning of the frame 2.

As a variant, the frame 2 can be freely mounted in rotation about the axis of rotation X. In this case, it is therefore the operator who manually rotates the frame 2 in order to place the screen 5 and the one-way mirror 4 in the suitable position.

When appropriate, whatever the embodiment, the instrument 1 can further comprise at least an abutment and/or an encoder configured to limit the travel of the frame 2 about the axis of rotation X. The abutment can be placed so as to limit the rotation of the frame 2 relative to its foot 3 to about 360°, in order to avoid damaging the cables connecting in a wired manner the different pieces of equipment of the instrument 1 to their respective power supply or to processing means.

Optionally, the image acquisition device 6 is secured in rotation to the at least partially light-blocking screen.

Figure 5:
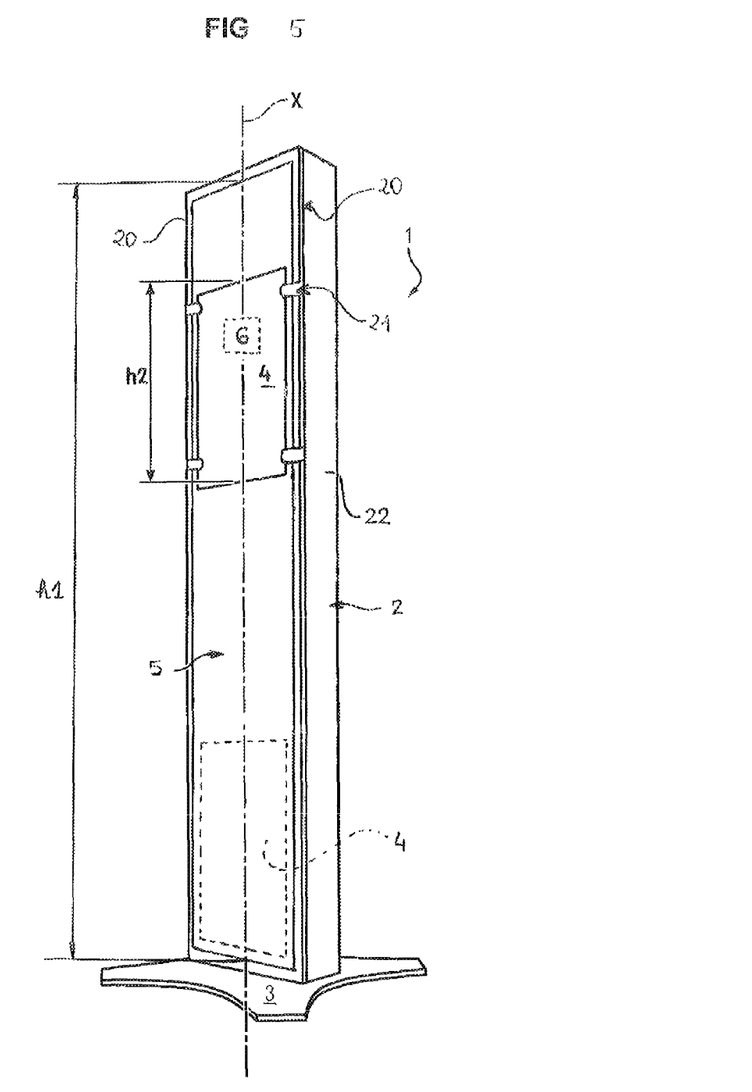
FIG. 5 is a front perspective view illustrating a second exemplary embodiment of a measuring instrument according to one embodiment of the invention, the one-way mirror being presented in front of the wearer.

In a second embodiment illustrated in FIG. 5, the reversible substitution of the one-way mirror 4 for the screen 5 can be carried out by the sliding of one relative to the other.

For example, the screen 5 and the one-way mirror 4 can be fixed on the frame 2 so as to extend substantially parallel relative to each other. One among the one-way mirror 4 and the screen 5—for example the screen 5 or according to FIG. 5, the one-way mirror—is then movably mounted in translation relative to the other—for example the one-way mirror 4 or according to FIG. 5, the screen 5—on sliders and the mask when placed in front. In this way, the substitution of the one-way mirror 4 for the screen 5 is carried out simply by translation of one of the elements (in the example, the screen 5 or according to the illustrated example, the one-way mirror 4) relative to the other (the one-way mirror 4 or according to the illustrated example, the screen 5) in order to allow its substitution without having to displace the instrument 1.

When appropriate, hinges 20 can be provided at the head of the instrument 1 or along the sections 22 of the frame 2 in order to allow the tilting of the element mounted in translation (for example, the screen 5 or according to the illustrated example, the one-way mirror 4), to free the entire surface of the fixed element (in the example, the one-way mirror 4) or according to the illustrated example, a major part of the surface of the screen 5 according to the illustrated example and to avoid disturbing the vision of the wearer during the measurements.

Preferably, the screen 5 is movably mounted in translation on sliders fixed on the frame 2 on either side of the one-way mirror 4, and at least partially conceals the one-way mirror 4 when it is placed in front. This indeed avoids having to displace the image acquisition device 6 and its actuator with the one-way mirror 4 during the substitution of the mirror for the screen 5.

On the contrary, according to the illustrated variant, it is the one-way mirror 4 that is movably mounted in translation on sliders 20 fixed on the frame 2 on either side of the one-way mirror 4, through complementary means 21 fixed on the lateral edges of the one-way mirror 4 and engaged in the sliders so as to ensure the translation of the one-way mirror 4 with respect to the frame. The one-way mirror 4 then at least partially conceals the screen 5 when it is placed in front. The fact of being able to place the one-way mirror 4 in front of the screen 5 allows the latter to be able to benefit from a maximum height h1 (for example substantially that of the column or that of the column from which the height of the one-way mirror 4 would be subtracted).

The dotted line in this figure represents the inactive position of the one-way mirror 4 in which it frees the major part of the screen 5 by being disposed following its translation along the sliders, in the lower part of the frame. In this example, the screen 5 has a height substantially equal to that of the column and its display can be dimensioned on the visible height of the screen when the one-way mirror 4 occupies the inactive position.

In this embodiment where the one-way mirror 4 is the movable element, the device for taking measurements 6 can be either fixed with respect to the frame or movable in vertical translation with respect to the frame and in this case optionally made secured in translation to the one-way mirror 4.

It is also possible to take advantage of the translational mobility of the one-way mirror 4 and of the measuring device 6, as well as possibly of either of the assemblies formed by the infrared light source 14, the infrared cameras 15 and/or the rotating arms, in order to adjust the height of this measuring assembly to the size of the concerned subject.

Optionally, the image acquisition device 6 is secured in translation to the at least partially light-blocking screen.

The instrument 1 may comprise other pieces of equipment allowing the operator to make various measurements of parameters necessary for the production of corrective glasses.

These parameters comprise, in a manner known per se, one at least of the following parameters: the pupillary half-distances, the height of the eyes of the wearer relative to the lower edge of the lens or of the glass frame, the vertex distance, the position of the center of rotation of the eye relative to the lens, the tilt angle (which corresponds to the measurement of the inclination of the mean plane of the corrective lens about a horizontal axis, relative to the vertical. It is an oriented angle which reflects the fact that the subject tends to have his face more or less raised or lowered when he looks at an object placed straight in front of his), the curve and the heading angle (which corresponds to the measurement of the angle of rotation about a vertical axis of the plane formed by the two nasal segments of the frame. The heading is an oriented angle which reflects the fact that the subject tends to have his face more or less turned left or right when he looks at an object placed straight in front of him), the parameters defining the dimension of the rectangles encompassing the lenses (sides A and B) and their relative position (side D and curve).

For this purpose, the instrument 1 can further comprise at least one of the following pieces of equipment:
- at least one visual target 9, 10, 11, 12, 13,
- at least one infrared light source 14 and at least one infrared camera 15,
- at least one speaker to give oral instructions to the user without visually entertaining him,
- at least one lighting strip 16,
- ground marking means 18.

The at least one visual target may comprise a LED emitting in the visible spectrum. For example, the instrument 1 can comprise:
- A first visual target 9 mounted on the frame 2 behind the one-way mirror 4 and emitting light rays in the direction of the face of the wearer through the one-way mirror 4. Preferably, this first visual target 9 is secured in movement to the image acquisition device 6 so as to be positioned substantially in front of the face of the wearer.
- Two second visual targets 10 mounted on the frame 2 behind the one-way mirror 4, in the upper part and in the lower part of the frame 2, respectively, by being substantially centered thereon and on the image acquisition device 6, and/or two third visual targets 11 mounted on the frame 2 on either side of the one-way mirror. The second and third visual targets 11 may each comprise a LED emitting in the visible spectrum. They can in particular be used so as to induce a spontaneous up/down or right/left displacement of the head of the wearer in order to bring him into his natural reference posture, unconstrained by his environment. When appropriate, the instrument 1 may comprise a fourth visual target 12 of the LED type emitting in the visible spectrum, centered on the frame 2 and allowing bringing the face of the wearer in front of the frame 2 between two diversions. Reference may be in particular made to document FR 2 961 608 in the name of the Applicant for more details on the determination of the natural reference posture of a wearer and the equipment necessary for this determination. Optionally, the two second visual targets 10 can be fixed on two retractable arms mounted on the frame 2 in order to shift them relative to the image acquisition device 6 and to increase the displacement of the face of the wearer. For example, the third visual targets 11 can be positioned on the arms so that an angle between the axis of the gaze of the wearer when he stares at each third visual target and the axis of his gaze when he stares at the fourth visual target 12 is on the order of 20°. Preferably, the retractable arms and the fourth visual target 12 are secured in movement and movable in translation along the vertical axis so as to adjust their height according to the size of the wearer. When appropriate, the retractable arms can be secured in movement to the image acquisition device 6.
- Two fifth visual targets 13 mounted on the frame 2 on either side of the one-way mirror 4 and each being able to comprise a LED emitting in the visible spectrum. They can in particular be used for determining the position of the center of rotation of the eyes of the wearer, from his corneal reflections. Reference may in particular be made to document WO 2016/075372 for an example of determination of the position of the center of rotation from the corneal reflections. When appropriate, the two fifth visual targets 13 can be fixed on the retractable arms, between the one-way mirror 4 and the third visual target. As a variant, the two third visual targets 11 can be optionally used for determining the center of rotation of the eyes of the wearer, instead of the fifth visual targets 13.
- At least one infrared light source 14, comprising for example an infrared LED, preferably three infrared LEDs, aligned and placed in the vicinity of the image acquisition device 6. This infrared light source 14 is associated with two infrared cameras 15 fixed on either side of the one-way mirror 4, either on the retractable arms or in the vicinity of the edges of the frame 2. The assembly formed by the infrared light source 14 and the infrared cameras 15 can then be used in order to acquire images of the wearer's glasses and measure parameters, such as the parameters defining the dimension of the rectangles encompassing the lenses (sides A and B) and their relative position (side D and curve). Advantageously, the combined use of a image acquisition device 6 in the visible range and in the infrared range allows guaranteeing the acquisition of images on which the frames of the glasses are clearly visible, some frames being infrared-transparent frames or not visible. On the images taken by a video camera. For example, the infrared cameras 15 can be placed so as to form an angle of +10° and −10° with respect to a plane of symmetry of the instrument 1. When appropriate, the infrared light source 14 and the infrared cameras 15 may be secured in movement to the image capture device so as to adjust their height according to the size of the wearer.

Preferably, the instrument 1 comprises a vertical lighting strip 16 on either side of the one-way mirror 4, said strips 16 being configured to light up the face of the wearer upon capture of the images by the image acquisition device 6. For example, the vertical lighting strips 16 can comprise strips of LEDs each mounted on a corresponding flap 17 fixed by means of hinges on either side of the one-way mirror 4 so as to be able to be opened or closed according to the needs of the operator. Each flap 17 can be displaced manually by the operator, or alternatively by a dedicated motor.

Figure 1:
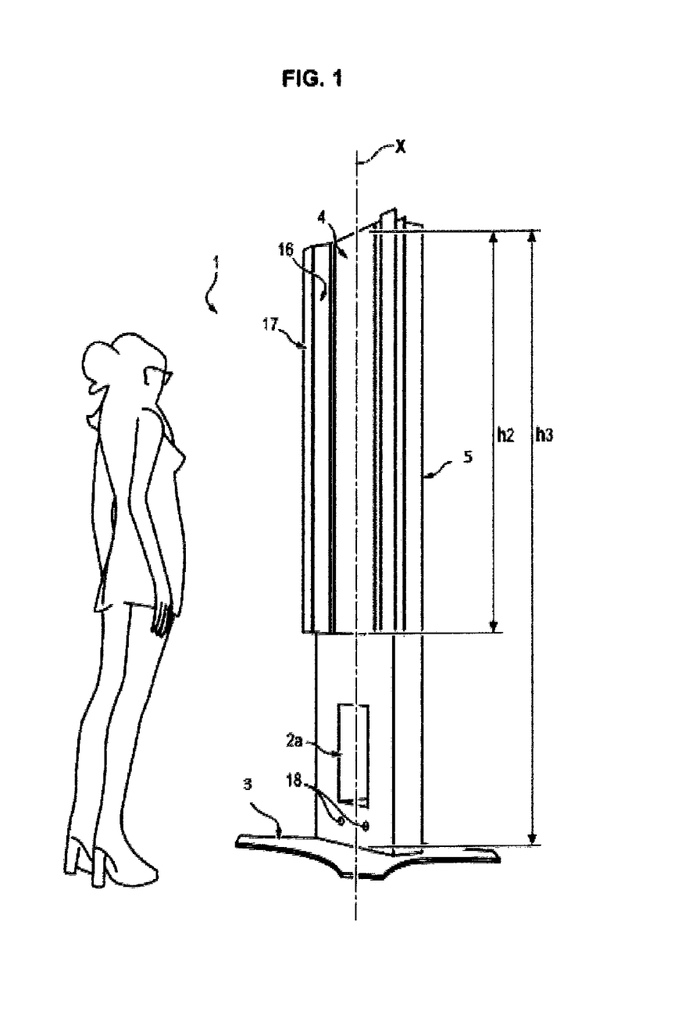
FIG. 1 is a front perspective view illustrating an exemplary embodiment of a measuring instrument according to one embodiment of the invention, the one-way mirror being presented in front of the wearer.
Figure 2:
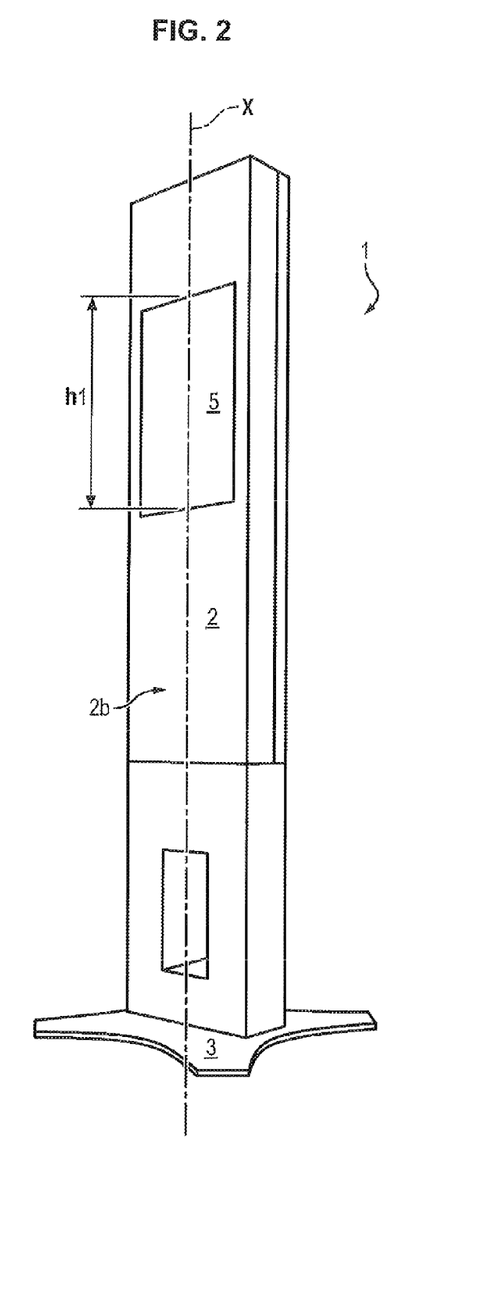
FIG. 2 is a rear perspective view of the example of the measuring instrument of FIG. 1.

The ground marking means 18 can comprise at least one, preferably two lasers mounted on the frame 2 and configured so as to point towards an area of the ground corresponding to the ideal location of the wearer relative to the instrument 1. These means 18 thus allow guaranteeing the positioning of the wearer and contribute to the accuracy of the measurement so that the images taken by the image acquisition device 6 and/or the infrared cameras 15 have optimum sharpness. Advantageously, the marking means 18 are fixed on the frame 2 so as to accompany the instrument 1 in its possible displacements and to automatically shift the area of the ground according to the new position of the instrument 1 (see FIGS. 1 and 3). When appropriate, the laser(s) can be used to project a logo or a marketing image on the ground area.

Alternatively, the marking means 18 comprise a sign placed manually on the ground by the operator.

Figure 4:
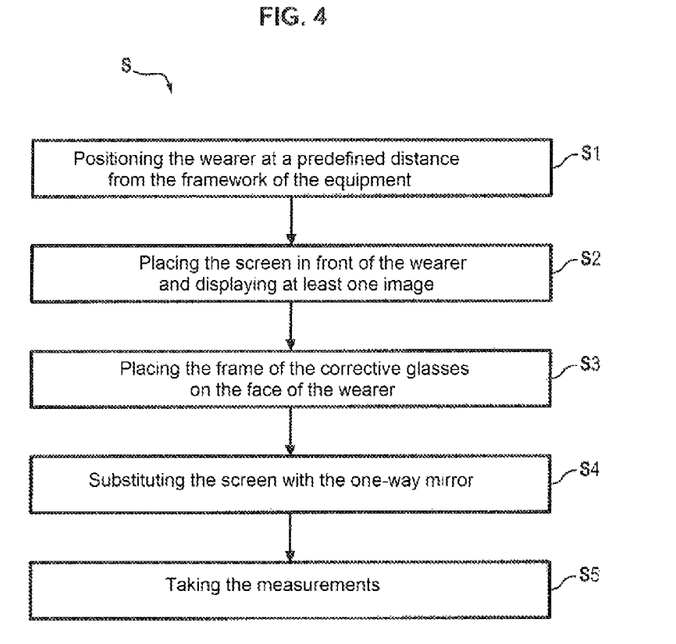
FIG. 4 is a flowchart illustrating different steps of a method for taking measurements of parameters necessary for the production of corrective glasses according to one embodiment of the invention and which can be implemented using a measuring instrument according to the invention.

Taking measurements of parameters necessary for the production of corrective glasses can then be carried out in accordance with the following steps:

S1: positioning the wearer at a predefined distance from the frame 2 of the instrument 1, S2: placing the screen 5 in front of the wearer and displaying at least one image, S3: placing a frame on the face of the wearer, S4: substituting the screen 5 with the one-way mirror 4, S5: taking the measurements.

More specifically, during the first step S1, the wearer is placed at an optimum distance from the instrument 1, and more particularly from the image acquisition device 6.

For example, the wearer can stand on the area indicated on the ground by the marking means 18.

During the second step S2, the screen 5 is placed in front of the wearer.

Generally, the screen 5 is already positioned so that it faces the wearer, since it can be used for marketing purposes in the optical store. The operator therefore simply makes sure that the screen 5 is in front of the wearer and not inclined relative to him.

Alternatively, the instrument 1 can be positioned so that the wearer is in front of the one-way mirror 4. In this case, thanks to the substitution means 8, the operator substitutes the screen 5 for the one-way mirror 4, for example by pivoting the frame 2 about the axis of rotation X until the screen 5 faces the wearer, or alternatively by sliding the screen 5 over the one-way mirror 4.

The wearer can then look at the screen 5 and place himself in a comfortable posture, without being hindered by the operator. Indeed, since the operator can remotely monitor the instrument 1 using the touch tablet 7, he does not need to be in the wearer's field of vision. In addition, the Applicant noticed that the wearer could be intimidated by his image in the one-way mirror 4, which had the effect of distorting the tilt and heading angle measurements since the wearer was not in his reference posture.

During this phase, the wearer can wear his corrective glasses so as to clearly view the images displayed on the screen 5, relax and naturally stand in his reference posture. At the same time, the operator can observe the wearer, monitor and possibly correct the position of his face and enter preliminary data on the frame or the wearer. The images projected by screen 5 can comprise an animation explaining the measuring process and what is expected from the wearer during these measurements.

During the third step S3, the wearer removes his corrective glasses and puts on the frame for which the parameters are to be measured. This step is performed without the wearer moving.

When appropriate, an accessory can be placed on the frame beforehand in order to facilitate the measurements. An example of an accessory has for example been described in document FR 2 719 463 and comprises, for example, a horizontal elongated support configured to be put on the upper border of the frame, a rod which extends vertically from the support and a protruding part which extends horizontally, perpendicularly to the support and to the rod. Targets comprising for example a colored marker and/or geometric shapes are fixed on these different parts so that the identification of the targets in the images taken by the image acquisition device 6 allows, knowing the relative position of the targets on the accessory, determining the spatial configuration of the frame.

During the fourth step S4, which can be simultaneous beforehand with the third step S3, the one-way mirror 4 is substituted for the screen 5, by rotation about the axis of rotation X or by sliding in the sliders.

During the fifth step S5, the measurements of the parameters necessary for the production of the corrective glasses are made using the image acquisition device 6 and all or part of the visual targets 9-15 and/or all or part of the infrared cameras 15 and infrared light sources 14.

For example, the first visual target 9 can be turned on so that the wearer focuses his gaze thereon, and one or more images of the face of the wearer are acquired by the image acquisition device 6 and/or by the infrared cameras 15. Vision parameters of the wearer can then be determined in accordance with the method described in document FR 2 860 887.

The wearer can also be brought into his reference posture using the second and third visual targets 10, 11 and possibly the fourth visual target 12, in accordance with the method described in document FR 2 961 608 mentioned above or in document FR 2 950 984 in the name of the Applicant.

The center of rotation of the eyes of the wearer can moreover be determined using the fifth visual targets 13, in accordance with the method described in document WO 2016/075372 mentioned above.

Once the measurements have been made, the operator can then store the touch tablet 7 in the storage space arranged in the frame 2.

The invention claimed is:

1. A measuring instrument comprising:
   a frame having a foot configured to stably hold the measuring instrument;
   a first screen mounted on the frame, wherein the first screen at least partially blocks light;
   a second screen mounted on the frame;
   an image acquisition device mounted on the frame so as to be concealed by the first screen;
   a pivot link coupled to the frame and configured to reversibly substitute the first screen with the second screen when moving from a measurement phase, wherein the first screen is positioned in front of a wearer, to a positioning phase, wherein the second screen is positioned in front of the wearer, by rotating the frame about an axis of rotation relative to the foot; and
   at least one of an abutment member or an encoder configured to limit travel of the frame about the axis of rotation.

2. The measuring instrument according to claim 1, wherein the first screen is fixed on a first face of the instrument and the second screen is fixed on a second face of the instrument which is distinct from the first face.

3. The measuring instrument of claim 1, further comprising a wireless monitoring device configured to send instructions to the image acquisition device and to the second screen.

4. The measuring instrument according to claim 3, further comprising a storage space formed in the frame and configured to contain the wireless monitoring device.

5. The measuring instrument of claim 1, wherein a height of the screen is comprised between 30% and 100% of a height of the first screen.

6. The measuring instrument of claim 1, wherein a height of the frame is comprised between 1.80 m and 2.20 m, a height of the first screen is comprised between 0.90 m and 2.0 m, and a height of the screen is comprised between 0.30 m and 1.60 m.

7. A measurement method comprising:
   positioning a wearer at a predefined distance from a frame of a measuring instrument, the frame having a foot configured to stably hold the measuring instrument;
   positioning a second screen of the measuring instrument in front of the wearer and displaying at least one image;
   placing a spectacle frame on a face of the wearer;
   substituting the second screen with a first screen of the measuring instrument by rotating the frame about an axis of rotation relative to the foot via a pivot link and limiting travel of the frame about the axis of rotation via at least one of an abutment member or an encoder, wherein the first screen at least partially blocks light; and
   acquiring images through the first screen and measuring parameters of the spectacle frame and of the wearer to produce corrective lenses.

8. The method according to claim 7, wherein the first screen is fixed on a first face of the instrument and the second screen is fixed on a second face of the instrument.

9. The instrument of claim 1, wherein a height of the frame is comprised between 1.80 m and 2.20 m, a height of the first screen is comprised between 0.90 m and 1.60 m, and a height of the screen is comprised between 0.30 m and 1.60 m.

10. The instrument of claim 1, wherein first screen comprises a one-way mirror.

* * * * *